United States Patent [19]
Hsieh

[11] Patent Number: 5,732,118
[45] Date of Patent: Mar. 24, 1998

[54] METHODS AND APPARATUS FOR IMAGE RECONSTRUCTION IN A MULTISLICE COMPUTED TOMOGRAPHY SYSTEM

[75] Inventor: Jiang Hsieh, Waukesha, Wis.

[73] Assignee: General Electric Company, Milwaukee, Wis.

[21] Appl. No.: 755,892

[22] Filed: Dec. 2, 1996

[51] Int. Cl.$^6$ .................................................. A61B 6/03
[52] U.S. Cl. ........................................... 378/19; 378/901
[58] Field of Search ........................................ 378/19, 901

[56] References Cited

U.S. PATENT DOCUMENTS 5,241,576  8/1993  Lonn ................................. 378/19
5,430,784  7/1995  Ribner et al. .................... 378/19

*Primary Examiner*—David P. Porta
*Assistant Examiner*—David Vernon Bruce
*Attorney, Agent, or Firm*—John S. Beulick; John H. Pilarski

[57] ABSTRACT

The present invention, in one form, is a system for obtaining data measurement signals for producing a tomographic image of an object in a multislice scan. More specifically, detector cells in at least one channel of a detector array are electrically coupled, or ganged, so that the ganged channel provides one data measurement signal to be transmitted through the gantry slip ring. The signal distribution in the z-direction for the ganged channel is then determined using signals obtained by adjacent non-ganged detector cells.

19 Claims, 2 Drawing Sheets

METHODS AND APPARATUS FOR IMAGE RECONSTRUCTION IN A MULTISLICE COMPUTED TOMOGRAPHY SYSTEM

FIELD OF THE INVENTION

This invention relates generally to computed tomography (CT) imaging and more particularly, to detector configuration and image reconstruction in a multislice CT system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Multislice CT systems are used to obtain data for an increased number of slices during a scan. Known multislice systems typically include detectors generally known as 2-D detectors. With such 2-D detectors, a plurality of detector cells form separate columns, or channels, and the columns are arranged in rows. Each row of detectors forms a separate slice. For example, a two slice detector has two rows of detector cells, and a four slice detector has four rows of detector cells. During a multislice scan, multiple rows of detector cells are simultaneously impinged by the x-ray beam, and therefore data for several slices is obtained.

Until now, it was believed that to add slices, i.e., rows of detector cells, to a CT system, significant hardware and software modifications are necessary. Particularly, a data acquisition system typically samples analog data from each detector cell and converts the data to digital signals for subsequent processing. Therefore, when adding detector cell rows to a detector array, the data acquisition system must be modified to sample data from the additional detector cells. Accordingly, for a two slice system, the data acquisition system must be modified to sample twice as many detector cells compared to a single slice system. Similarly, for a four slice system, the data acquisition system must be modified to sample four times as many detector cells compared to a single slice system.

Furthermore, by increasing the number of detector cells, the mount of data which must be transmitted across the gantry slip ring is increased. Such increased data preferably is transmitted across the slip ring within the same time frame at which data from a system with fewer detector cells is transmitted, and therefore, where increasing the number of detector cells, the data transmission rate across the slip ring typically must be increased.

It is desirable add detector cell rows to a CT system without requiring significant modifications, both software and hardware, to known systems. It also would be desirable to provide such a multi-row system without degrading overall image quality.

SUMMARY OF THE INVENTION

These and other objects may be attained in a multislice system which, in one embodiment, includes a partially ganged detector array. Particularly, and in accordance with one embodiment of the present invention, at least one channel of a multi-channel detector array is ganged so that such channel transmits only one data measurement signal when impinged by an x-ray beam. In one form, detector cells in at least one column of cells, or channel, are combined, or ganged, in the z-direction so that for the ganged cells, one channel signal is transmitted from the detector cells through the slip ring. Other detector cells in adjacent channels are not ganged so that such detector cells provide separate data measurement signals. More specifically, the ganged detector cells are positioned between two non-ganged detector cells. In another form, the ganging is achieved by utilizing a single detector cell which is twice as long as other cells in the z direction.

The signal distribution in the z-direction for the transmitted ganged channel signal is determined using signals obtained from the adjacent non-ganged detector cells. Particularly, and for a two slice system having detector rows A and B, the signal distribution in the z-direction for the ganged channel, i, is estimated in accordance with the following:

$$S'_{Ai} = \frac{\delta_{A(i-1)} + \delta_{A(i+1)}}{2} S_i$$

$$S'_{Bi} = \frac{\delta_{B(i-1)} + \delta_{B(i+1)}}{2} S_i$$

where:

$$\delta_{Ai} = \frac{S_{Ai}}{S_{Ai} + S_{Bi}};$$

$$\delta_{Bi} = \frac{S_{Bi}}{S_{Ai} + S_{Bi}};$$

$S_i$ is the signal obtained from, e.g., transmitted from, ganged channel i;

$S_{Ai}$ is a non-ganged detector cell signal obtained from channel i for detector row A;

$S_{Bi}$ is a non-ganged detector cell signal obtained from channel i for detector row B;

$S'_{Ai}$ is an estimated ganged detector cell signal at channel i for detector row A; and $S'_{Bi}$ is an estimated ganged detector cell signal at channel i for detector row B.

By ganging channels as described above, additional detector cell rows may be added to a CT system without requiring significant hardware and software modifications to known systems. In addition, such ganging is not believed to reduce overall image quality.

DETAILED DESCRIPTION OF THE DRAWINGS

Figure 1:
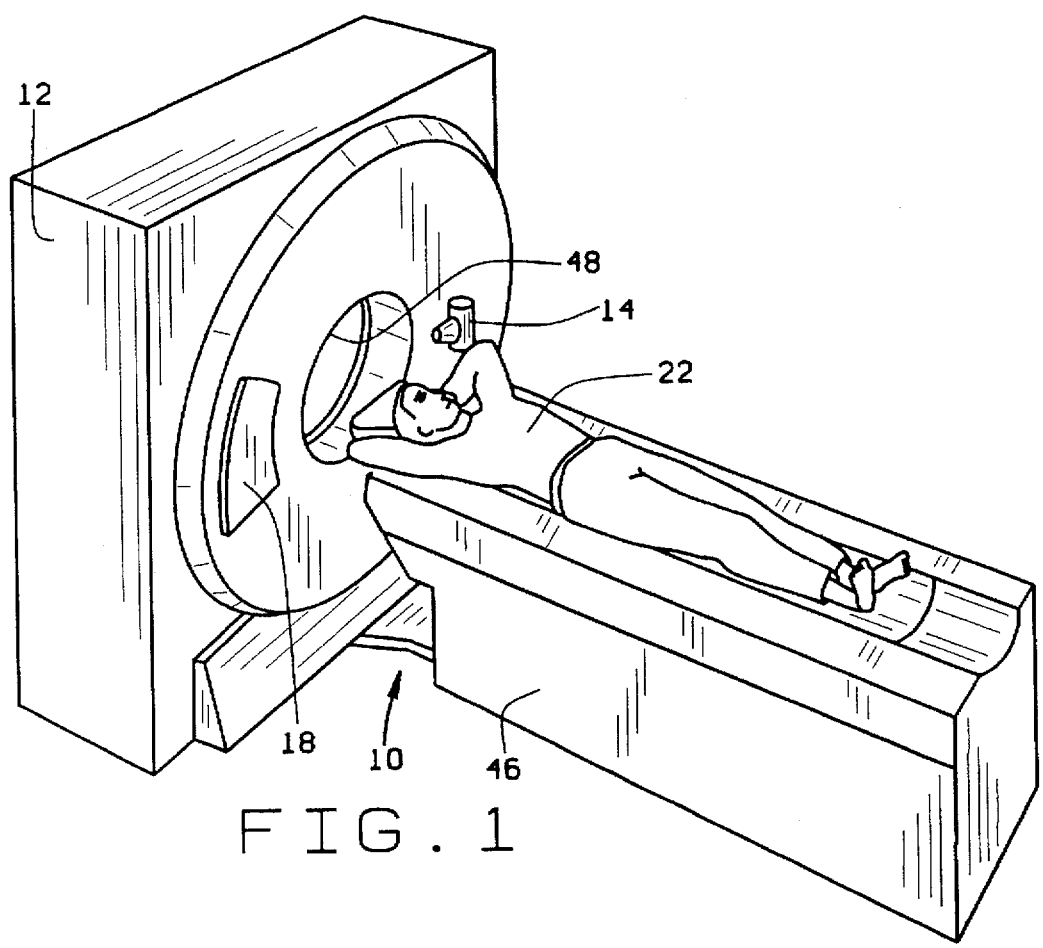
FIG. 1 is a pictorial view of a CT imaging system.
Figure 2:
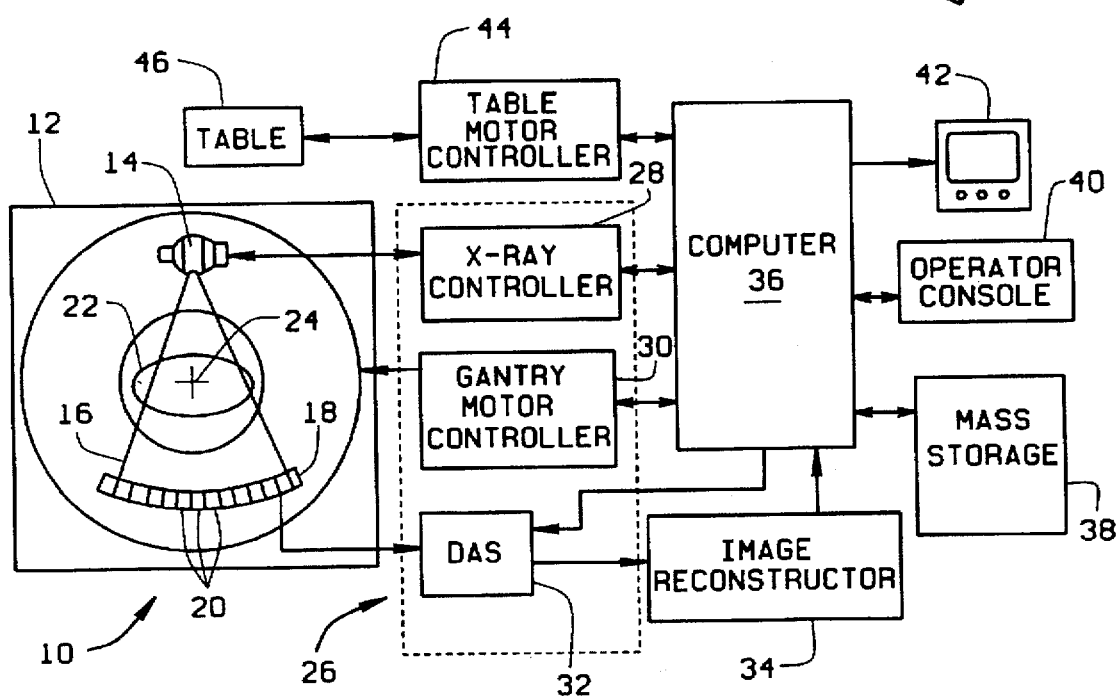
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on both the fan angle and view angle.

The following discussion of signal estimation, image quality, and ganged detector arrays sometimes refers specifically to multislice CT scanners, which typically include detector arrays have two, four, or more rows of detector elements, or detector cells. The ganged detector arrays and signal estimation, however, are not limited to practice in connection with only two and four slice scanners and may be used with other multislice CT scanners having more or fewer detector cell rows. Moreover, the present signal estimation is not directed to any particular helical image reconstruction algorithm. Rather, the present signal estimation may be used in conjunction with many different types of helical weighting factors. In addition, the present signal estimation may be used in conjunction with axial scans, i.e., in a step-and-shoot mode. Further, in one embodiment, the signal estimation would be implemented in computer 36 and would process, for example, data stored in mass storage 38. Many other alternative implementations are, of course, possible.

Figure 3:
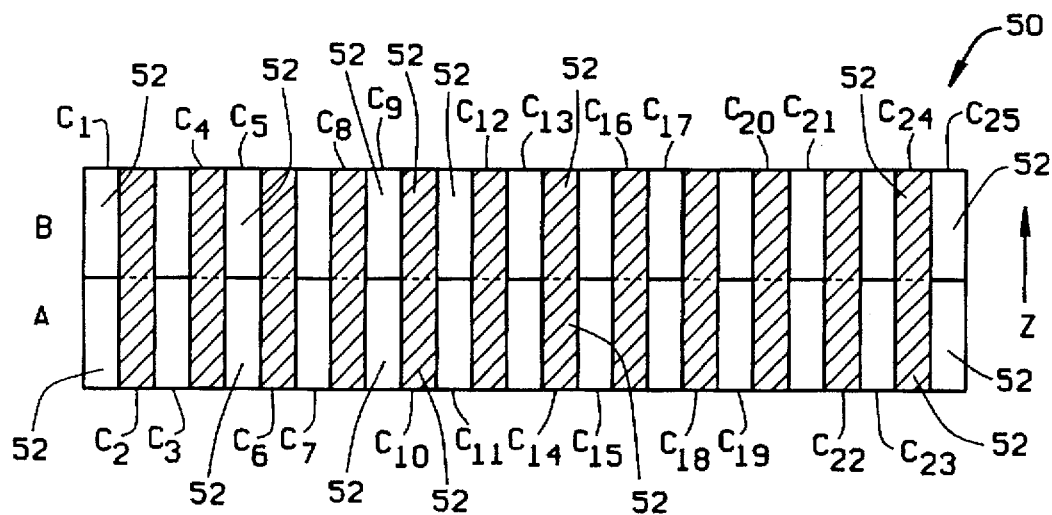
FIG. 3 is a schematic diagram of a two slice detector array in accordance with one embodiment of the present invention.

FIG. 3 illustrates a two slice, or twin system, detector array 50 in accordance with one embodiment of the present invention. Detector array 50 is a 2-D detector array having two rows, A and B, of detector cells 52 displaced in the z-direction. Each column of detector cells 52 in the z-direction defines a channel $C_1$–$C_{25}$. Accordingly, FIG. 3 illustrates a twin system having twenty five (25) channels.

Detector cells 52 in at least one of channels $C_1$–$C_{25}$ are "ganged", or combined in the z-direction. Specifically, twelve (12) channels $C_2$, $C_4$, $C_6$, $C_8$, $C_{10}$, $C_{12}$, $C_{14}$, $C_{16}$, $C_{18}$, $C_{20}$, $C_{22}$, and $C_{24}$ include ganged detector cells 52. The channels including ganged detector cells are sometimes referred to herein as ganged channels. The remaining thirteen (13) channels $C_1$, $C_3$, $C_5$, $C_7$, $C_9$, $C_{11}$, $C_{13}$, $C_{15}$, $C_{17}$, $C_{19}$, $C_{21}$, $C_{23}$, and $C_{25}$, however, include non-ganged detector cells 52. The channels including non-ganged detector cells are sometimes referred to herein as non-ganged channels. Each ganged channel $C_2$, $C_4$, $C_6$, $C_8$, $C_{10}$, $C_{12}$, $C_{14}$, $C_{16}$, $C_{18}$, $C_{20}$, $C_{22}$, and $C_{24}$ is positioned between two non-ganged channels $C_1$, $C_3$, $C_5$, $C_7$, $C_9$, $C_{11}$, $C_{13}$, $C_{15}$, $C_{17}$, $C_{19}$, $C_{21}$, $C_{23}$, and $C_{25}$. For example, ganged channel $C_2$ is between non-ganged channels $C_1$ and $C_3$. Similarly, ganged channel $C_{10}$ is between non-ganged channels $C_9$ and $C_{11}$.

For a scan, detector cells 52 of each non-ganged channel $C_1$, $C_3$, $C_5$, $C_7$, $C_9$, $C_{11}$, $C_{13}$, $C_{15}$, $C_{17}$, $C_{19}$, $C_{21}$, $C_{23}$, and $C_{25}$ generate separate data measurement signals, i.e., each non-ganged detector cell 52 generates a data measurement signal. However, detector cells 52 of each ganged channel $C_2$, $C_4$, $C_6$, $C_8$, $C_{10}$, $C_{12}$, $C_{14}$, $C_{16}$, $C_{18}$, $C_{20}$, $C_{22}$, and $C_{24}$ generate only one combined data measurement signal per channel. These data measurement signals may be stored, for example, in DAS 32. Accordingly, for one view of a scan, detector array 50 generates only thirty eight (38) detector data measurement signals.

To reconstruct images for each slice, i.e., for each row A and B, the signal distribution in the z-direction for each ganged channel $C_2$, $C_4$, $C_6$, $C_8$, $C_{10}$, $C_{12}$, $C_{14}$, $C_{16}$, $C_{18}$, $C_{20}$, $C_{22}$, and $C_{24}$ is determined. Specifically, and before generating images, separate data measurement signals are estimated for each detector cell 52 in row A and row B of ganged channels $C_2$, $C_4$, $C_6$, $C_8$, $C_{10}$, $C_{12}$, $C_{14}$, $C_{16}$, $C_{18}$, $C_{20}$, $C_{22}$, and $C_{24}$.

The signal distribution, in one form, is determined by interpolating the data measurement signals obtained from detector cells 52 of non-ganged channels $C_1$, $C_3$, $C_5$, $C_7$, $C_9$, $C_{11}$, $C_{13}$, $C_{15}$, $C_{17}$, $C_{19}$, $C_{21}$, $C_{23}$, and $C_{25}$. The data measurement signals obtained from detector cells 52 in row A of non-ganged channels $C_1$, $C_3$, $C_5$, $C_7$, $C_9$, $C_{11}$, $C_{13}$, $C_{15}$, $C_{17}$, $C_{19}$, $C_{21}$, $C_{23}$, and $C_{25}$ are interpolated to estimate separate data measurement signals for ganged detector cells 52 in row A of channels $C_2$, $C_4$, $C_6$, $C_8$, $C_{10}$, $C_{12}$, $C_{14}$, $C_{16}$, $C_{18}$, $C_{20}$, $C_{22}$, and $C_{24}$. Similarly, the data measurement signals obtained from detector cells 52 in row B of non-ganged channels $C_1$, $C_3$, $C_5$, $C_7$, $C_9$, $C_{11}$, $C_{13}$, $C_{15}$, $C_{17}$, $C_{19}$, $C_{21}$, $C_{23}$, and $C_{25}$ are interpolated to estimate separate data measurement signals for ganged detector cells 52 in row B.

As one specific example, each ganged channel i generates one combined data measurement signal, $S_i$. The signal distribution in the z-direction for each ganged channel i is estimated in accordance with the following:

$$S'_{Ai} = \frac{\delta_{A(i-1)} + \delta_{A(i+1)}}{2} S_i \quad (1)$$

$$S'_{Bi} = \frac{\delta_{B(i-1)} + \delta_{B(i+1)}}{2} S_i$$

where:

$$\delta_{Ai} = \frac{S_{Ai}}{S_{Ai} + S_{Bi}} ; \quad (2)$$

$$\delta_{Bi} = \frac{S_{Bi}}{S_{Ai} + S_{Bi}} ;$$

$S_{Ai}$ is a non-ganged detector cell signal obtained from channel i for detector row A;

$S_{Bi}$ is a non-ganged detector cell signal obtained from channel i for detector row B;

$S'_{Ai}$ is an estimated ganged detector cell signal at channel i for detector row A; and $S'_{Bi}$ is an estimated ganged detector cell signal at channel i for detector row B.

Accordingly, separate data signal measurement estimations $S'_{Ai}$ for each row A and $S'_{Bi}$ for each row B of ganged channels $C_2$, $C_4$, $C_6$, $C_8$, $C_{10}$, $C_{12}$, $C_{14}$, $C_{16}$, $C_{18}$, $C_{20}$, $C_{22}$, and $C_{24}$ are acquired.

While the above-described interpolation is a linear interpolation, other order interpolations may be used. For example, second order or even higher order interpolation may used. It is believed that higher order interpolation may preserve a higher frequency component of each data signal measurement contributing to the estimated signal measurements.

The signal estimations $S'_{Ai}$ and $S'_{Bi}$ are then used in conjunction with the generated non-ganged data measurement signals to generate an image of the object. Particularly, signal estimations $S'_{Ai}$ and data measurement signals generated by detector cells 52 in row A of non-ganged channels $C_1$, $C_3$, $C_5$, $C_7$, $C_9$, $C_{11}$, $C_{13}$, $C_{15}$, $C_{17}$, $C_{19}$, $C_{21}$, $C_{23}$, and $C_{25}$ are processed to generate an image slice for row A of detector cells 52. Similarly, signal estimations $S'_{Bi}$ and data measurement signals generated by detector cells 52 in row B of non-ganged channels $C_1$, $C_3$, $C_5$, $C_7$, $C_9$, $C_{11}$, $C_{13}$, $C_{15}$, $C_{17}$, $C_{19}$, $C_{21}$, $C_{23}$, and $C_{25}$ are processed to generate an image slice for row B of detector cells 52. The signal estimations and data measurement signals may be processed, for example, in accordance with the filtered back projection technique.

As one specific example, the signal distribution in the z-direction, i.e., for row A and row B, for ganged channel $C_2$ is determined in accordance with the separate data measurement signals obtained by detector cells 52 of non-ganged channels $C_1$ and $C_3$. Particularly, signals generated by detector cells 52 in row A of non-ganged channels $C_1$ and $C_3$ each contribute to estimating the separate data measurement signal at detector cell 52 in row A of ganged channel $C_2$. Similarly, signal measurements obtained by detector cells 52 in row B of non-ganged channels $C_1$ and $C_3$ each contribute to estimating the data measurement signal at detector cell 52 in row B of ganged channel $C_2$.

Ganged channel signal estimation may be performed after CT system 10 calibration. For example, the signal estimation may be performed after beam hardening.

The above-described detector array 50 and ganged signal estimation reduces data transmission rates in twin slice helical image reconstruction and facilitates adding rows of detector cells to a single slice CT system. Particularly, and as explained above, detector cells 52 of array 50 generate only thirty eight (38) data measurement signals, rather than the fifty data measurement signals typically generated in a twenty five (25) channel twin slice system. Accordingly, with the above twin slice system, DAS 32 merely samples 1.5 times the amount of data sampled in a single slice system. Moreover, it is believed that such twin slice system does not significantly reduce image quality.

Ganged detector channels $C_2$, $C_4$, $C_6$, $C_8$, $C_{10}$, $C_{12}$, $C_{14}$, $C_{16}$, $C_{18}$, $C_{20}$, $C_{22}$, and $C_{24}$, as described above, each include two detector cells 52. However, such description is exemplary only, and is not limiting. For example, each ganged detector channel $C_2$, $C_4$, $C_6$, $C_8$, $C_{10}$, $C_{12}$, $C_{14}$, $C_{16}$, $C_{18}$, $C_{20}$, $C_{22}$, and $C_{24}$ may consist of one elongate detector cell, which is approximately about twice as long as each non-ganged detector cell 52 in the z-direction. In this embodiment, each elongate, i.e., ganged, detector cell generates one data measurement signal, $S_i$, and the z-distribution of such signal can be estimated as described above.

While the above-described embodiment includes a plurality of ganged channels in a twin slice system, it is to be understood that there are many variations of this configuration. For example, fewer than twelve or more than twelve channels may be ganged. Similarly, and rather than ganging every other channel, every third or every fourth channel could be ganged. Also, such ganging could be performed on a four slice system, or on any multi-slice system. In addition, more than every other channel may be ganged.

Figure 4:
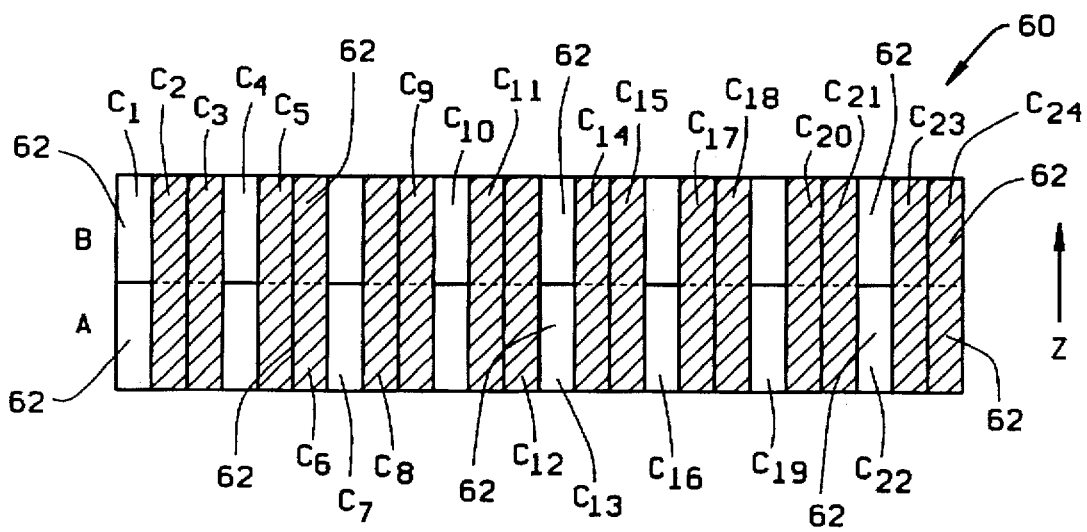
FIG. 4 is a schematic diagram of a two slice detector array in accordance with another embodiment of the present invention.

FIG. 4 illustrates a twin system detector array 60 in accordance with another embodiment of the present invention. Detector array 60 includes two rows A and B of detector cells 62 configured in twenty four (24) channels $C_1$–$C_{24}$. Detector cells 62 in adjacent channels $C_2$ and $C_3$, $C_5$ and $C_6$, $C_8$ and $C_9$, $C_{11}$ and $C_{12}$, $C_{14}$ and $C_{15}$, $C_{17}$ and $C_{18}$, $C_{20}$ and $C_{21}$, and $C_{23}$ and $C_{24}$, respectively, are ganged, so that each such channel generates only one combined data measurement signal. However, detector cells 62 in remaining channels $C_1$, $C_4$, $C_7$, $C_{10}$, $C_{13}$, $C_{16}$, $C_{19}$, and $C_{22}$ are not ganged, and thus generate separate data measurement signals. Accordingly, during a scan, detector cells 62 of twin system detector array, 60 generate only thirty two (32) data measurement signals, rather than the forty eight (48) data measurement signals typically obtained in a twenty four channel twin slice system. Moreover, twin system detector array 60 generates only eight (8) more data measurement signals than a twenty four channel single slice system. Accordingly, DAS 32 merely samples 1⅓ times the amount of data sampled in a single slice system. The signal distribution in the z-direction for each ganged channel $C_2$, $C_3$, $C_5$, $C_6$, $C_8$, $C_9$, $C_{11}$, $C_{12}$, $C_{14}$, $C_{15}$, $C_{17}$, $C_{18}$, $C_{20}$, $C_{21}$, $C_{23}$, and $C_{24}$ may be estimated in accordance with equations (1) and (2).

Channel ganging, as explained above, facilitates adding rows of detector cells to CT systems without requiring substantial modifications to known systems. For example, as described above, the DAS need only be configured to sample eight additional signals when a second row of twenty four detector cells is added to a twenty four channel single slice system. Furthermore, and when channel ganging is used, a fifth row of detector cells may be added to a conventional four slice system without even modifying the DAS or slip-ting of such system.

As explained above, while the above-described embodiments reference twin slice scanners, other multislice scanners may be used. For example, multiple channels in a four slice scanner may be ganged. Similarly, and rather than adding a second row of detector cells to a single slice system, ganging may be used to add a nth row of detector cells to a n−1 system.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while the description herein references twin slice scanners, the present signal estimation may be used in connection with other slice scanners. Furthermore, while the signal estimation described above was a simple linear interpolation, the signal distribution in the z-direction may be estimated with higher orders of interpolation. Accordingly, the spirit and scope of the invention are to be limited only by the terms of the appended claims.

What is claimed is:

1. A system for obtaining data measured signals for producing a tomographic image of an object in a tomographic scan, said system comprising a detector array comprising:

at least one ganged detector cell channel; and at least one non-ganged detector cell channel;

said ganged detector cell channel comprising at least one detector cell and configured to provide one data measurement signal, said non-ganged detector cell channel comprising at least two detector cells and configured to provide at least two data measurement signals.

2. A system in accordance with claim 1 wherein said detector array comprises at least two rows of detector cells and wherein said ganged detector cell channel comprises at least two ganged detector cells.

3. A system in accordance with claim 2 further comprising at least two adjacent ganged detector cell channels.

4. A system in accordance with claim 2 wherein said ganged detector cell channels are between respective non-ganged detector cell channels.

5. A system in accordance with claim 2 further comprising at least two non-ganged detector cell channels, and wherein said ganged detector cell channel is between said non-ganged detector channels.

6. A system in accordance with claim 1 configured to determine a signal distribution in a z-direction for said ganged detector cell channel.

7. A system in accordance with claim 6 configured to determine said signal distribution in said z-direction in accordance with:

$$S'_{Ai} = \frac{\delta_{A(i-1)} + \delta_{A(i+1)}}{2} S_i$$

$$S'_{Bi} = \frac{\delta_{B(i-1)} + \delta_{B(i+1)}}{2} S_i$$

where:

$$\delta_{Ai} = \frac{S_{Ai}}{S_{Ai} + S_{Bi}} ;$$

$$\delta_{Bi} = \frac{S_{Bi}}{S_{Ai} + S_{Bi}} ;$$

$S_i$ is a signal obtained from ganged channel i;

$S_{Ai}$ is a non-ganged detector cell signal obtained from channel i for detector row A;

$S_{Bi}$ is a non-ganged detector cell signal obtained from channel i for detector row B;

$S'_{Ai}$ is an estimated ganged detector cell signal at channel i for detector row A; and $S'_{Bi}$ is an estimated ganged detector cell signal at channel i for detector row B.

8. A system in accordance with claim 1 wherein said ganged detector cell channel comprises one detector cell.

9. A system in accordance with claim 8 wherein said ganged detector cell channel is between respective non-ganged detector cell channels.

10. A system in accordance with claim 8 configured to determine a signal distribution in a z-direction for said ganged detector cell channel.

11. A system in accordance with claim 10 configured to determine said signal distribution in said z-direction in accordance with:

$$S'_{Ai} = \frac{\delta_{A(i-1)} + \delta_{A(i+1)}}{2} S_i$$

$$S'_{Bi} = \frac{\delta_{B(i-1)} + \delta_{B(i+1)}}{2} S_i$$

where:

$$\delta_{Ai} = \frac{S_{Ai}}{S_{Ai} + S_{Bi}} ;$$

$$\delta_{Bi} = \frac{S_{Bi}}{S_{Ai} + S_{Bi}} ;$$

$S_i$ is a signal obtained from ganged channel i;

$S_{Ai}$ is a non-ganged detector cell signal obtained from channel i for a detector row A;

$S_{Bi}$ is a non-ganged detector cell signal obtained from channel i for a detector row B;

$S'_{Ai}$ is an estimated ganged detector cell signal at channel i for a detector row A; and $S'_{Bi}$ is an estimated ganged detector cell signal at channel i for a detector row B.

12. A detector array for a multislice computed tomography system, said detector array comprising at least one ganged channel and at least one non-ganged channel, said ganged channel comprising at least one detector cell, and said non-ganged channel comprising at least two detector cells.

13. A detector array in accordance with claim 12 wherein said ganged channel comprises one detector cell.

14. A detector array in accordance with claim 12 further comprising two rows of detector cells, and wherein said ganged channel comprises at least two ganged detector cells.

15. A method for obtaining data measurement signals in a multislice computed tomography system, the system including a detector array having at least two channels, said method comprising:

obtaining one signal from at least one gaged channel of the detector array; and determining a signal distribution in a z-direction for the ganged channel.

16. A method in accordance with claim 15 wherein each channel includes at least two detector cells, and wherein obtaining one signal from one ganged channel comprises the step of summing the outputs of the detector cells of the one ganged channel.

17. A method in accordance with claim 15 wherein the ganged channel comprises one detector cell having a z-axis length approximately about equal to the z-axis length of the other channels formed by a plurality of detector cells, and obtaining one signal from the ganged channel comprises obtaining an output signal from the one cell.

18. A method in accordance with claim 15 wherein each channel includes at least two detector cells, and wherein obtaining one signal from at least one ganged channel comprises the step of summing the detector cell outputs of every other channel so that one signal is provided for every other channel.

19. A method in accordance with claim 15 wherein determining a signal distribution in the z-direction for the ganged channel is performed in accordance with:

$$S'_{Ai} = \frac{\delta_{A(i-1)} + \delta_{A(i+1)}}{2} S_i$$

$$S'_{Bi} = \frac{\delta_{B(i-1)} + \delta_{B(i+1)}}{2} S_i$$

where:

$$\delta_{Ai} = \frac{S_{Ai}}{S_{Ai} + S_{Bi}};$$

$$\delta_{Bi} = \frac{S_{Bi}}{S_{Ai} + S_{Bi}};$$

$S_i$ is a signal obtained from ganged channel i;

$S_{Ai}$ is a non-ganged detector signal obtained from channel i of a detector row A;

$S_{Bi}$ is a non-ganged detector signals obtained from channel i of a detector row B;

$S'_{Ai}$ is an estimated ganged detector cell signal at channel i of detector row A; and $S'_{Bi}$ is an estimated ganged detector cell signal at channel i of detector row B.

* * * * *